United States Patent [19]

Uji

[11] Patent Number: 4,931,475
[45] Date of Patent: Jun. 5, 1990

[54] CHOLAGOGUE AND/OR GALLSTONE SOLUBILIZER

[75] Inventor: Akira Uji, Hirakata, Japan

[73] Assignee: Hiya Pharmaceutical Co., Ltd., Osaka, Japan

[21] Appl. No.: 815,710

[22] PCT Filed: Apr. 21, 1984

[86] PCT No.: PCT/JP84/00208
§ 371 Date: Dec. 10, 1985
§ 102(e) Date: Dec. 10, 1985

[87] PCT Pub. No.: WO85/04804
PCT Pub. Date: Nov. 7, 1985

[51] Int. Cl.⁵ .............. A61K 33/05; A61K 31/23; A61K 31/225; A61K 31/335
[52] U.S. Cl. ...................... 514/729; 514/25; 514/511
[58] Field of Search ............ 514/25, 511, 729

[56] References Cited

U.S. PATENT DOCUMENTS

| | | | |
|---|---|---|---|
| 2,657,166 | 10/1953 | Stonecipher | 514/511 |
| 2,666,728 | 1/1954 | Smith | 514/511 |
| 3,181,151 | 5/1965 | Nordmann | 514/729 |
| 4,242,360 | 12/1980 | Pailer et al. | 514/729 |
| 4,767,783 | 8/1988 | Hara et al. | 514/729 |

FOREIGN PATENT DOCUMENTS

| | | | |
|---|---|---|---|
| 59441 | 9/1982 | European Pat. Off. | 514/511 |
| 3045483 | 12/1982 | Fed. Rep. of Germany | 514/511 |
| 48913 | 3/1982 | Japan | 514/25 |
| 108714 | 6/1984 | Japan | 514/511 |
| 991785 | 5/1965 | United Kingdom | 514/729 |

OTHER PUBLICATIONS

Chemical Abstracts, Apr. 26, 1982, vol. 96, No. 17, p. 87, 96: 135798u.
The Merck Index, ninth edition (1976), pp. 173 and 174.

Primary Examiner—J. E. Evans
Attorney, Agent, or Firm—Armstrong, Nikaido, Marmelstein, Kubovcik & Murray

[57] ABSTRACT

A cholagogic and/or gallstone solubilizer comprising a borneol compound as its active component.

6 Claims, 11 Drawing Sheets

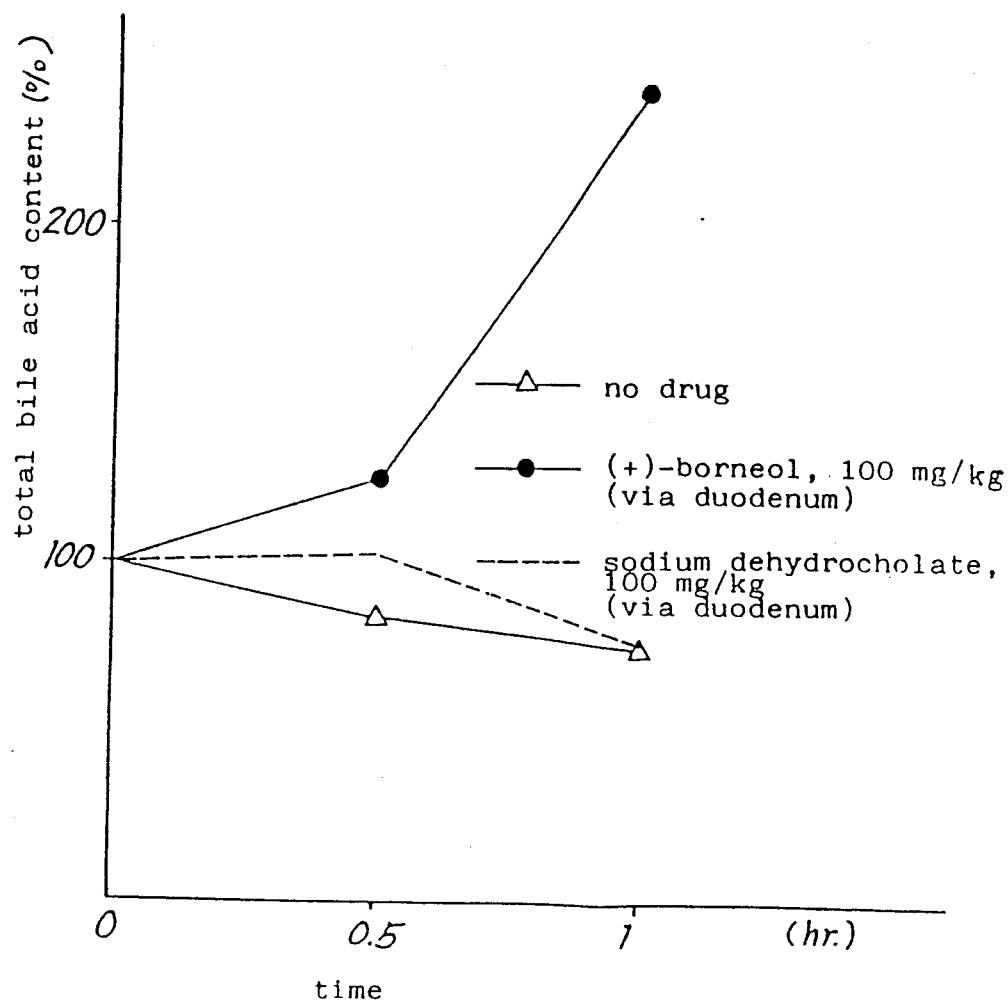
FIG. II

CHOLAGOGUE AND/OR GALLSTONE SOLUBILIZER

TECHNICAL FIELD

The present invention relates to a cholagogue and/or a gallstone solubilizer comprising a borneol compound as the active component thereof.

BACKGROUND ART

Unexpectedly, there are a wide variety of bile duct and gallbladder diseases which include cholangitis, cholecystitis, biliary dys-kinesia (bile filling up the gall bladder, discharge function disorder), cholelithiasis, etc., and these diseases not infrequently develop into chronic diseases. Operations encounter difficulties and do not always afford good results.

Accordingly, it is important to use cholagogues and like agents for causing bile to normally flow into the duodenum via the bile duct without stagnation, for preventing formation of gallstones and for dissolving gallstones for treatment.

We have carried out research on the medicinal efficacy of components of a Japanese traditional drug, "Kiogan", and found that (+)-borneol has a totally unexpected, strong and sustained activity to promote the flow of bile and to dissolve gallstones and further that other borneols also have similar activity. Thus, the present invention has been accomplished.

DISCLOSURE OF THE INVENTION

Borneols are generally in the form of white crystalline powder or blocks and have unique fragrance. The pharmacological activities of borneols are not known except that naturally occurring (+)-borneol is empirically known to have pharmacological activities such as analgesic, anti-inflammatory, sedative and anti-palpitation effects and central depressant activity because it has fragrance and has long been used in the oriental medicine under the name of "Ryuno".

With attention directed to the cholagogic activity and gallstone dissolving activity of borneol compounds which activities have not been heretofore known, the present invention provides a novel cholagogic and gallstone solubilizing agent which contains a borneol compound as its active component.

BRIEF DESCRIPTION OF THE DRAWINGS

FIG. 5 to FIG. 11 are graphs showing variations in the weight of solids, content of phospholipids, content of cholesterol, amounts of bile acids and total amount of bile acids in the secreted bile with the lapse of time when (+)-borneol or sodium dehydrocholate was intraduodenally administered to rats.

BEST MODE OF CARRYING OUT THE INVENTION

Figure 1:
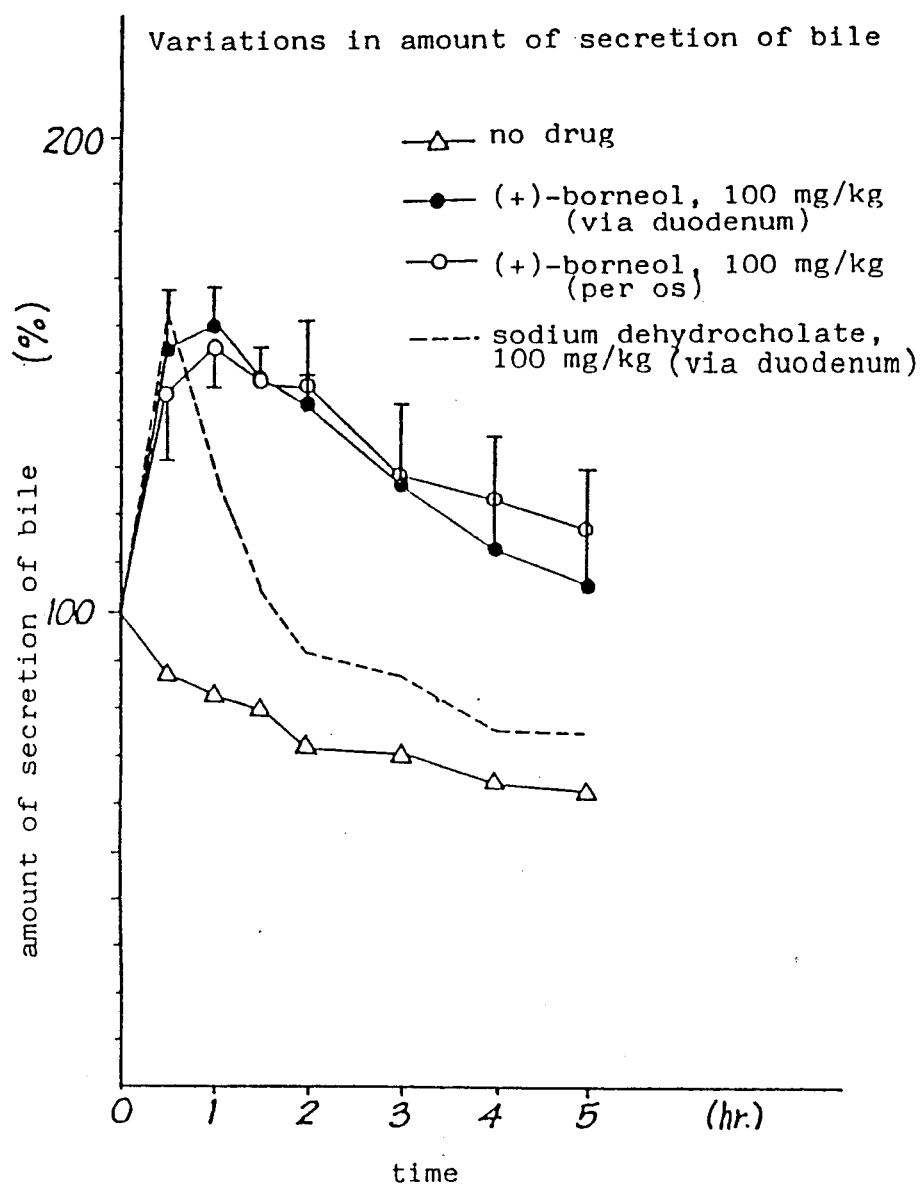
FIG. 1 is a graph showing variations in the amount of secreted bile with time when (+)-borneol was administered to rats intraduodenally or orally.

According to the present invention, the borneol compounds include the following.

a. Borneols such as (+)-borneol, (−)-borneol, (±)-borneol, (+)-isoborneol, (−)-isoborneol and (±)-isoborneol.

(+)-, (−)- and (±)-borneols are represented by the following structural formula and have a melting point of 204° to 208° C.

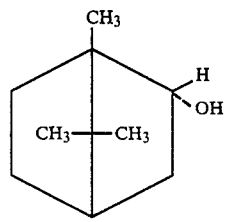

(+)-, (−)- and (±)-isoborneols are represented by the following structural formula and have a melting point of 212° to 214° C.

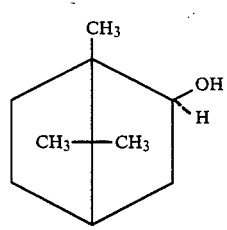

b. Esters of borneols with fatty acids (R—COOH wherein R is alkyl having 1 to 9 carbon atoms). The esterification reaction is represented by the following equation.

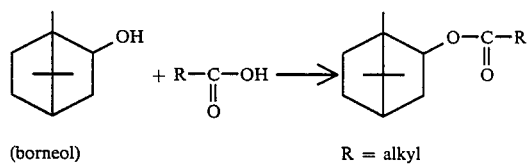

(borneol)　　　　　　　　　　R = alkyl

The following alkyl-containing acids are examples of useful fatty acids.

Acetic acid ($CH_3$—)
Propionic acid ($CH_3$—$CH_2$—)
n-Butyric acid ($CH_3$—$(CH_2)_2$—)
Isovaleric acid

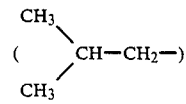

n-Caproic acid ($CH_3(CH_2)_4$—)
n-Enanthylic acid ($CH_3(CH_2)_5$—)
n-Caprylic acid ($CH_3(CH_2)_6$—)
n-Pelargonic acid ($CH_3(CH_2)_7$—)
n-Capric acid ($CH_3(CH_2)_8$—)

c. Esters of borneols with dicarboxylic acid (HOOC-$(CH_2)_n$—COOH where n is 2, 3 or 4).

Examples of useful dicarboxylic acids are as follows.
Succinic acid (HOOC—$(CH_2)_2$—COOH)
Glutaric acid (HOOC—$(CH_2)_3$—COOH)
Adipic acid (HOOC—$(CH_2)_4$—COOH)

d. Esters of borneols with hydroxycarboxylic acids.

Examples of useful hydroxycarboxylic acids are the following hydroxy polybasic acids.

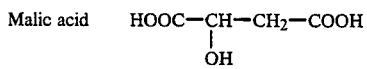

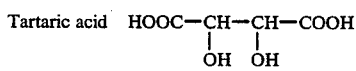

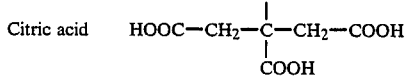

e. Glycosides of borneols

Examples of useful glycosides are as follows.

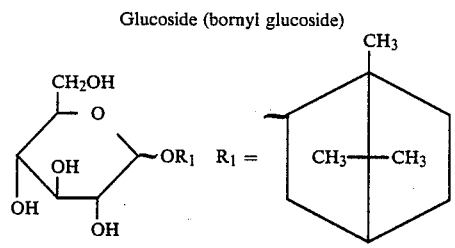

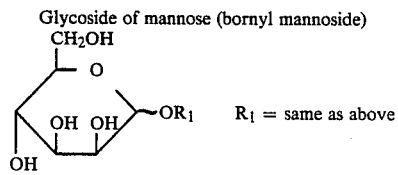

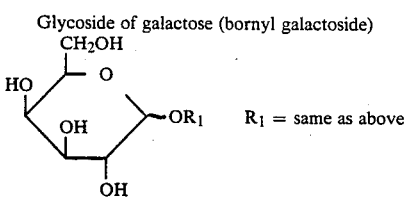

Described in detail below are medicinal efficacy tests and acute toxicity test performed for borneols for use as cholagogues, along with preparation examples.

Medicinal efficacy tests (1) Activity on the secretion of bile

A. Intraduodenal administration

Male Wister rats weighing 200 to 250 g were used, ten rats in each group. Each rat was fasted for 6 to 8 hours, and was thereafter fastened as laid on its back to a fixed table under ethereal anesthesia. The abdomen was cut open along the midline. A polyethylene tube was inserted into and attached to the common bile duct. The rat was then allowed to stand for a period of time (1 hour) to assure stabilized flow of bile. The amount of bile flowing out for the following period of 30 minutes was taken as 100 to serve as a control amount for the subsequent flow of bile.

Next, the drug to be tested was intraduodenally administered to the rat, and the amount of bile flowing out from the polyethylene tube dropwise was measured over a period of 5 hours. The amount was measured for every 30-minute period of the first 2 hours after the administration of the drug and then for every one-hour period. Sodium dehydrocholate, bile acid preparation serving as a known cholagogue, was used as a control drug.

Figure 2:
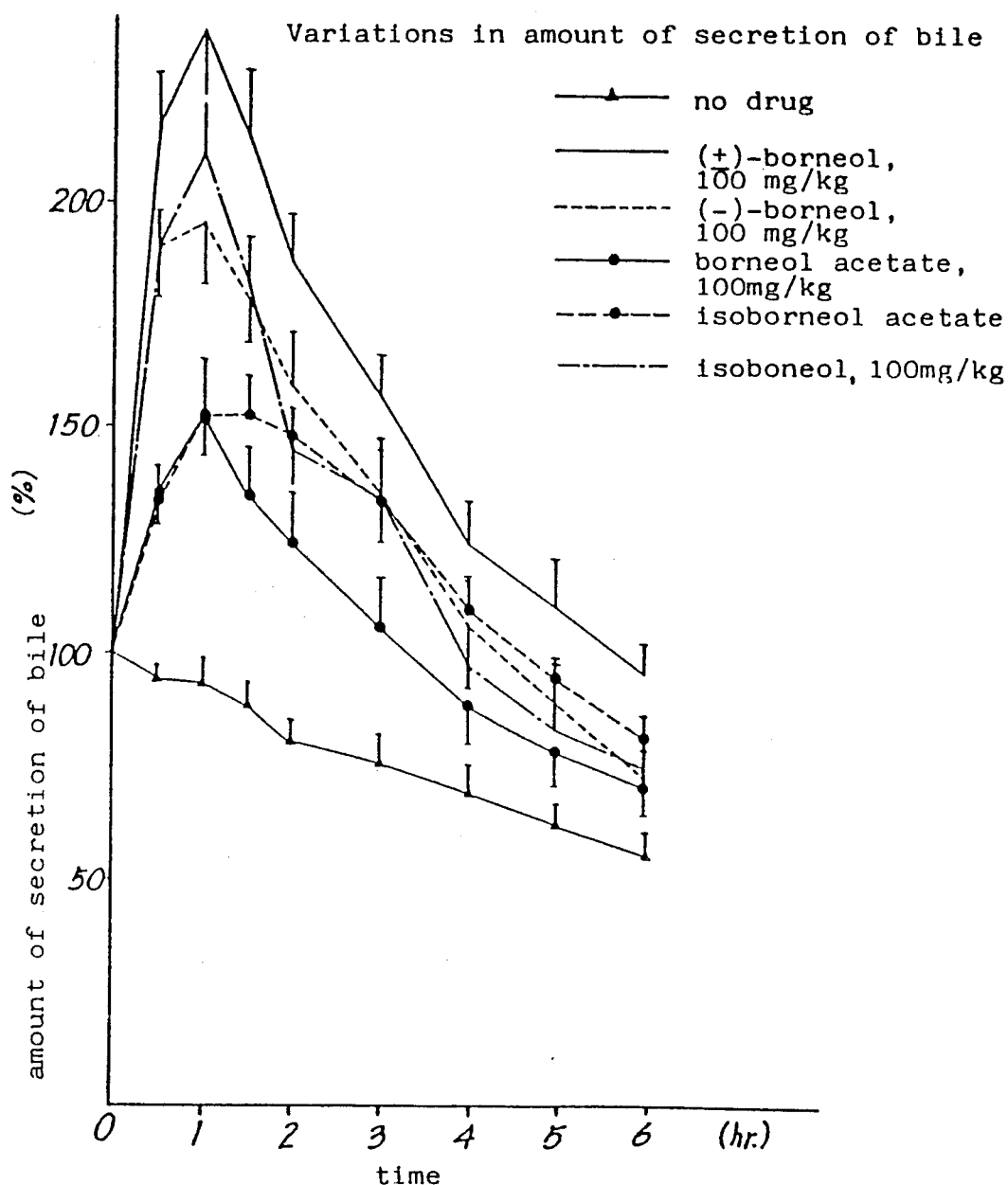
FIG. 2 is a graph showing variations in the amount of secreted bile with time when (−)-borneol, (±)-borneol, acetic acid ester of borneol, acetic acid ester of isoborneol or isoborneol was intraduodenally given to rats.
Figure 3:
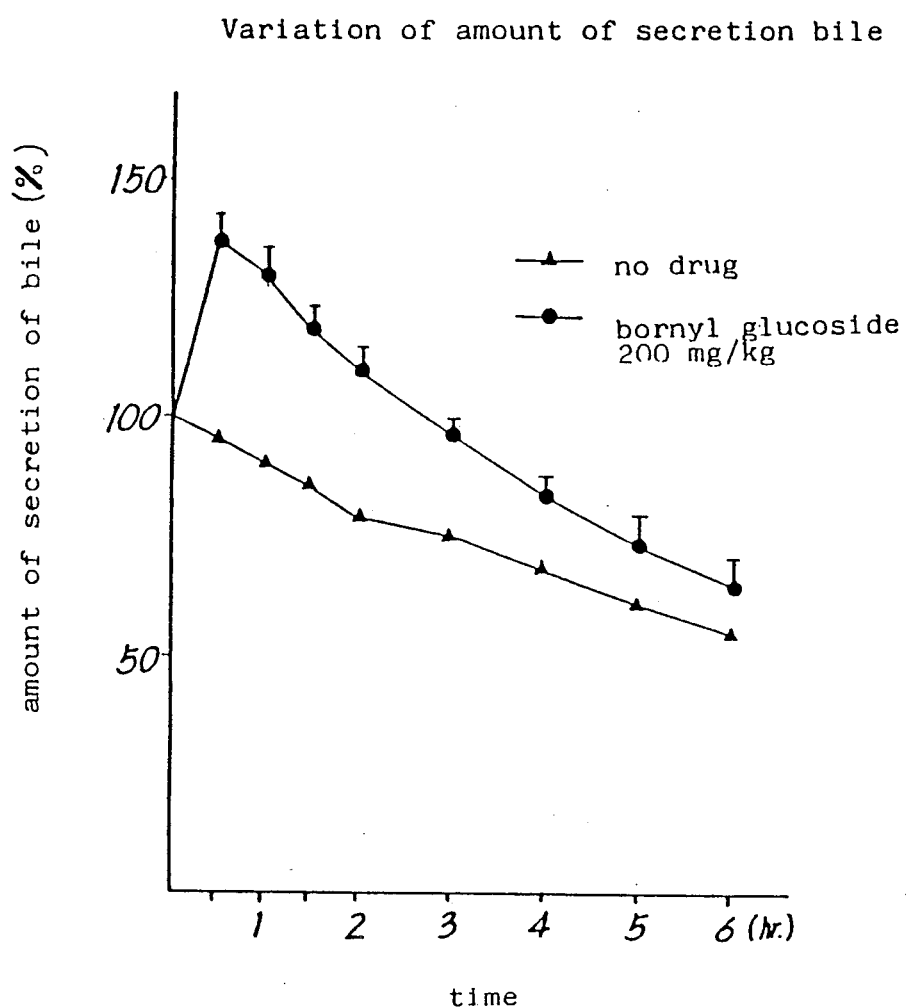
FIG. 3 is a graph showing variations in the amount of secreted bile with time when bornyl glucoside was intraduodenally administered to rats.

The dose was 200 mg/kg (weight of rat) for bornyl glucoside, or 100 mg (drug)/kg (weight of rat) for other borneols and sodium dehydrocholate. The drugs were used as suspended in 4% aqueous solution of gum arabic. Experimental results As shown in FIG. 1, the group to which 100 mg/kg of (+)-borneol was administered was apparently different in the mode of cholagogic effect from the control group to which sodium dehydrocholate was administered. Sodium dehydrocholate exhibited a transient great cholagogic effect 30 minutes after the administration, whereas (+)-borneol produced a sustained great cholagogic effect over the entire observation period of 5 hours. It was further found that (−)-borneol, (±)-borneol, isoborneol, bornyl acetate, isobornyl acetate and bornyl glucoside also had a cholagogic effect as in the case of (+)-borneol and were usable for the same purpose (FIG. 2 and FIG. 3).

B. Oral Administration

As in the case of intraduodenal administration, the drug to be tested was orally administered to rats each having a polyethylene tube attached to the common bile duct, and the amount of bile flowing out was observed over a period of 5 hours.

Experimental results

Figure 4:
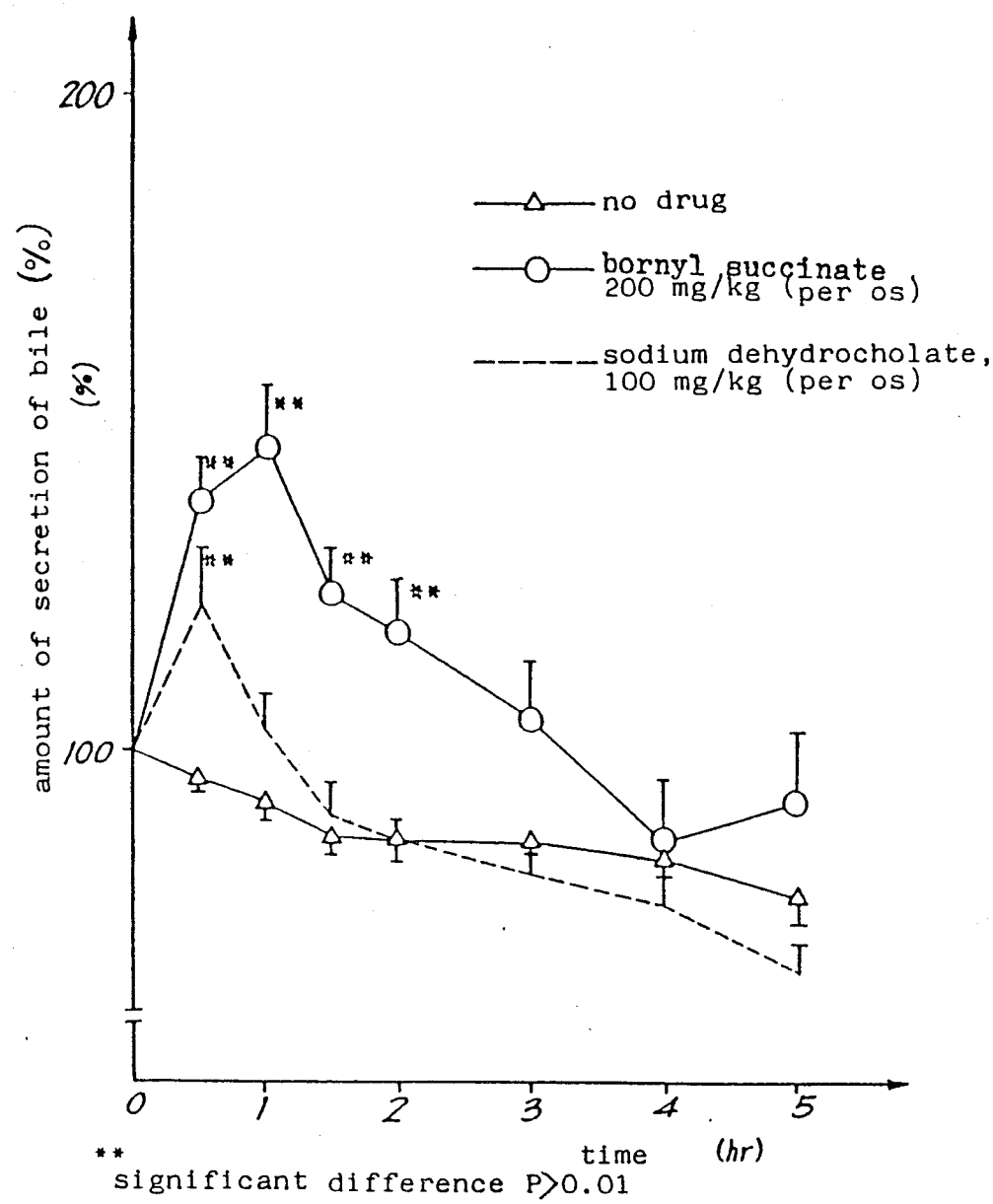
FIG. 4 is a graph showing variations in the amount of secreted bile with time when bornyl succinate was orally administered to rats.

FIG. 1 reveals that as in the case of intraduodenal administration, borneol apparently produced more sustained greater cholagogic effect than the control drug, i.e. sodium dehydrocholate. It was further found that bornyl succinate also had a cholagogic effect and was usable for the same purpose (FIG. 4).

(2) Cholagogic characteristics

A. Variations in the weight of solids in discharged bile

The bile portions obtained from the bile secretion experiment (1)-A by intraduodenal administration were collected respectively for the observation periods. A quantity of each bile portion was freeze-dried, and the solids weight was measured to determine the variations in the solids weight of bile over the 5-hour period. The solids weight of bile obtained during the 30-minute period before the administration of the test drug, e.g. (+)-borneol, was calculated as 100.

Experimental results

Figure 5:
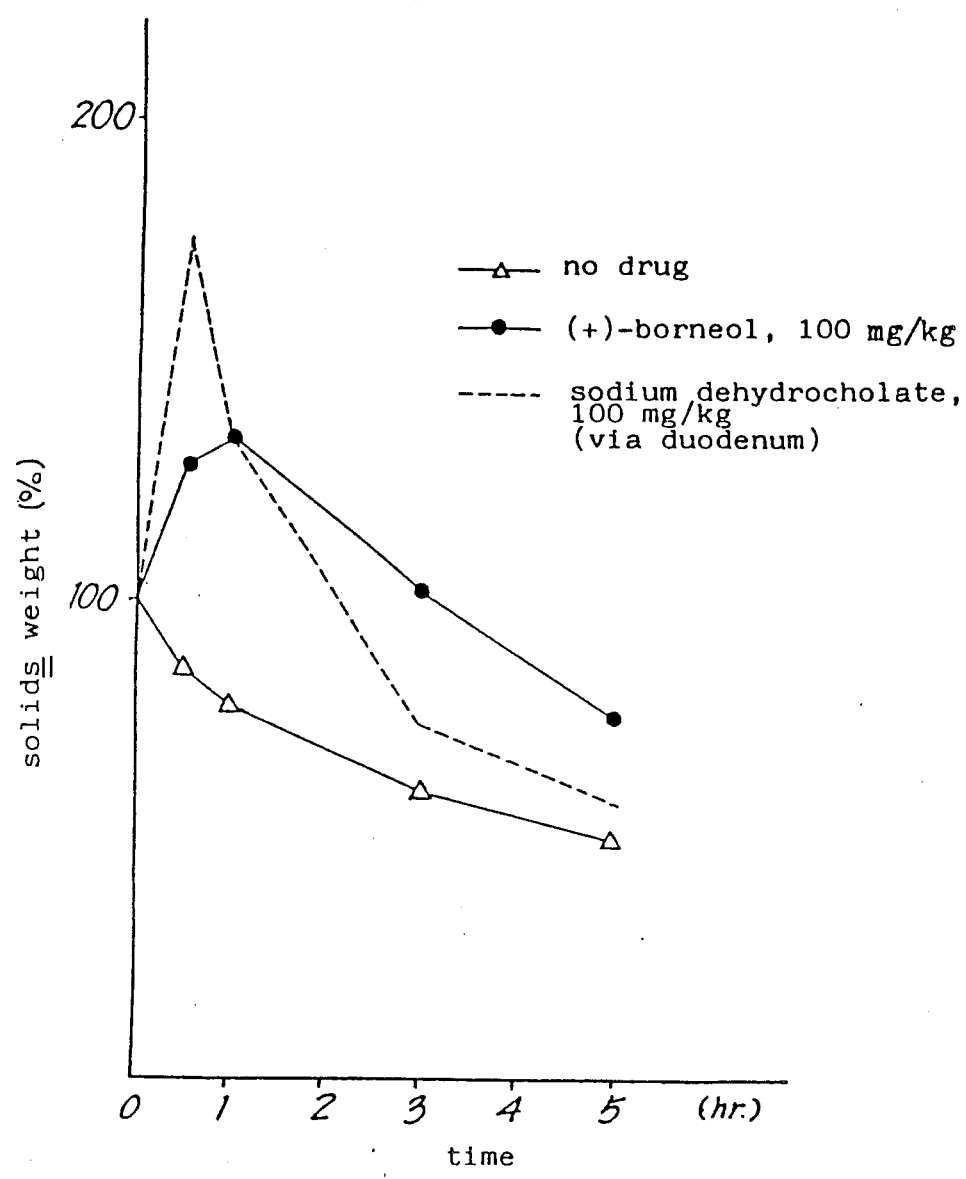

FIG. 5 showing the solids weight measurements of bile during the observation period of 5 hours reveals that (+)-borneol has a sustained effect to increase the amount of biliary constituents unlike the control drug, sodium dehydrocholate.

B. Variations in the phospholipid and cholesterol contents of bile

Portions of the bile obtained during the first one-hour period of measurement in the bile secretion experiment (1)-A by intraduodenal administration were tested for phospholipid using Phospholipid B-Test Wako (enzyme method, Wako Pure Chemical Industries Ltd.) and for cholesterol using Cholesterol CII-Test Wako measuring kit(COD-p-chlorophenol color development method, Wako Pure Chemical Industries Ltd.). For the quantitative determination of phospholipid and cholesterol, a blank test was conducted, and a calibration curve prepared in advanced was used. The phospholipid and cholesterol contents of the bile flowing out during the period of 30 minutes before the administration of the test drug were taken as 100.

Experimental results

Figure 6:
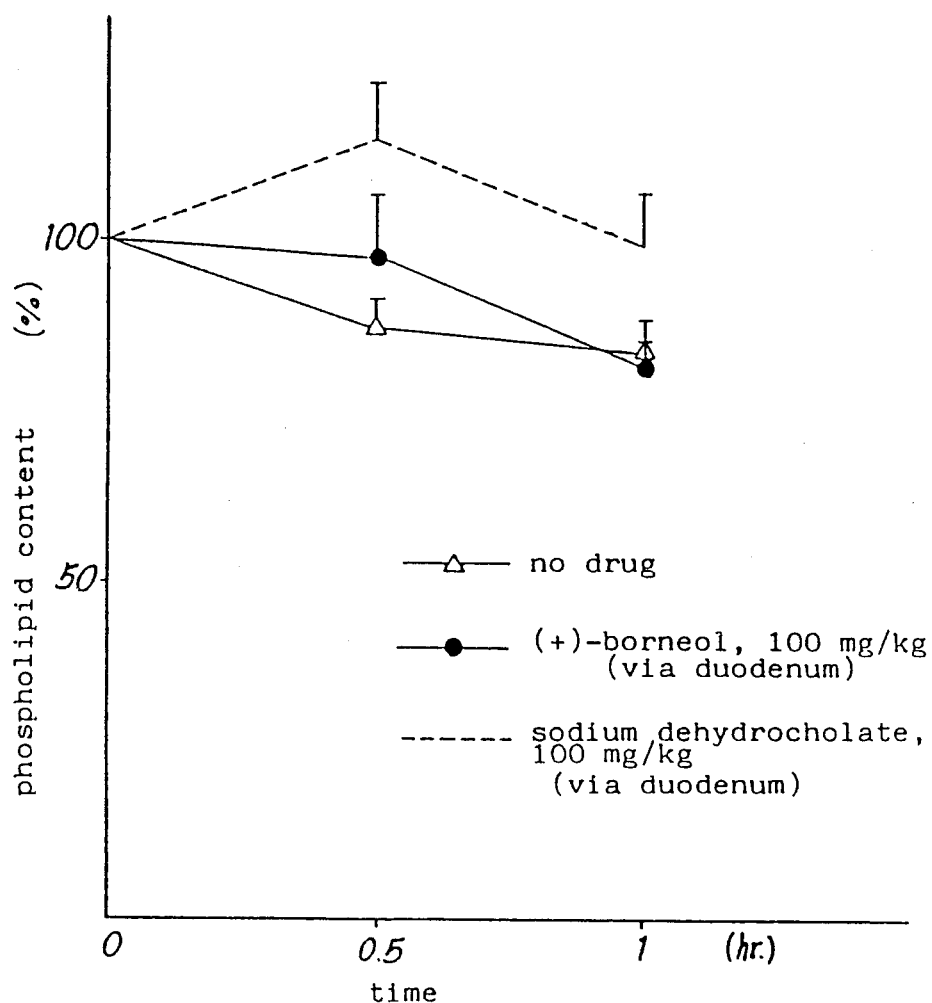
Figure 7:
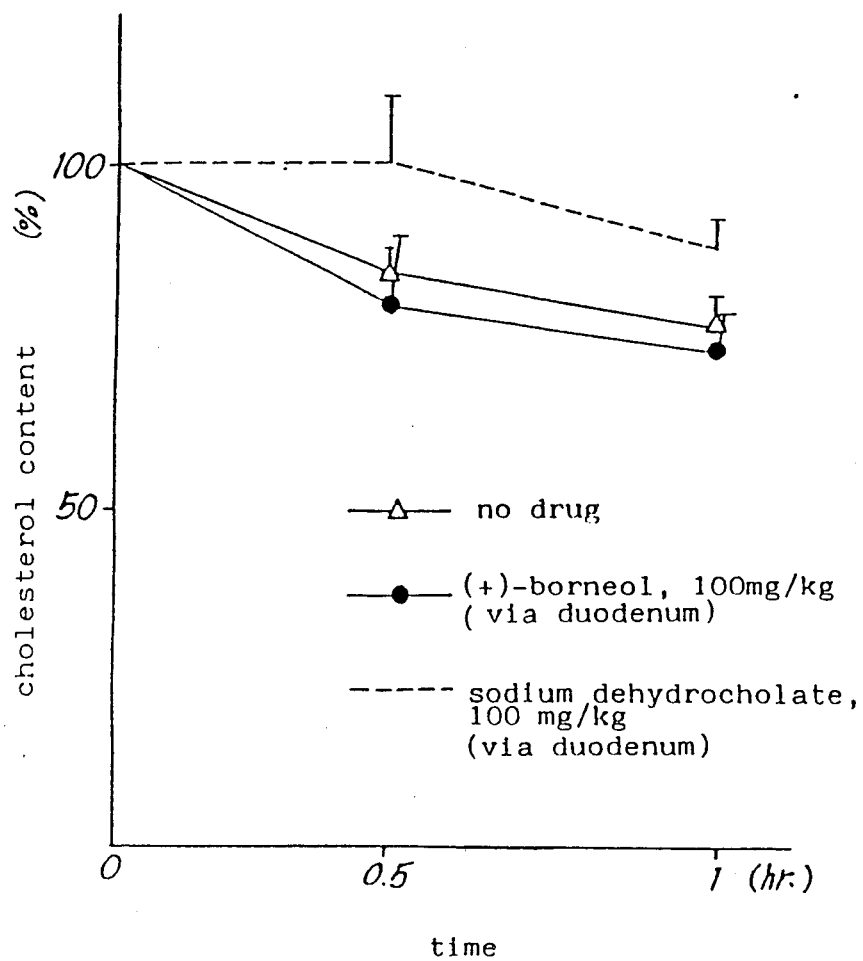

As shown in FIGS. 6 and 7, the group to which the control drug, i.e. sodium dehydrocholate, was administered exhibited a tendency for the phospholipid and cholesterol contents of bile to increase, whereas the group to which borneol was administered achieved the result that these contents were approximately at the same level as those of the normal bile.

C. Variations in bile acid contents of bile

The bile acids, which are important components of the bile of mammals, include cholic acid, chenodeoxycholic acid, deoxycholic acid and ursodeoxycholic acid. Only minor amounts of these acids are present in the free state. Usually they are dissolved in bile in the form of glycine conjugates or taurine conjugates.

These bile acids have the structural formula below and —OH group in positions 3, 7 12 as indicated below. The position of —OH group on the steroid nucleus is shown with a symbol $\alpha$ when on the lower side of the paper or with a symbol $\beta$ when on the upper side.

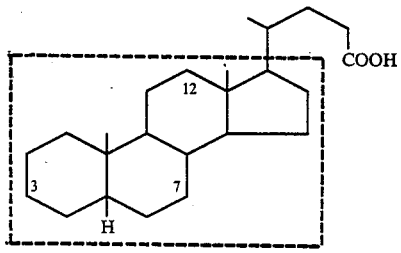

Cholic acid: 3($\alpha$), 7($\alpha$), 12($\alpha$)
Chenodeoxycholic acid: 3($\alpha$), 7($\alpha$)
Deoxycholic acid: 3($\alpha$), 12($\alpha$)
Ursodeoxycholic acid: 3($\alpha$), 7($\beta$)

The glycine conjugates and the taurine conjugates have the following structure wherein R2 is the portion of the foregoing structural formula of bile acids enclosed by a broken line.

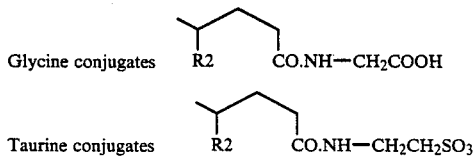

Bile was checked for variations in the contents of these bile acids.

Each portion of bile obtained during the first one-hour period of measurement in the foregoing bile secretion experiment (1)-A by intraduodenal administration was partly collected, then diluted 40-fold with freshly distilled methanol and thereafter filtered with use of a 0.45-micron membrane filter (product of Toyo Roshi). The filtrate was subjected to high-speed liquid chromatography according to the method of Okuyama S. et al., Chemistry Letters, p 1443 (1979). The bile acid contents of the bile flowing out during each measurement period were determined with reference to calibration curves prepared in advance for cholic acid, ursodeoxycholic acid, chenodeoxycholic acid and deoxycholic acid, and also for glycine conjugates and taurine conjugates of these acids. The total bile acid content was determined from the results. The bile acid contents and the total bile acid content of the bile flowing out during the period of 30 minutes before the administration of the test drug were taken as 100.

Experimental results

Figure 8:
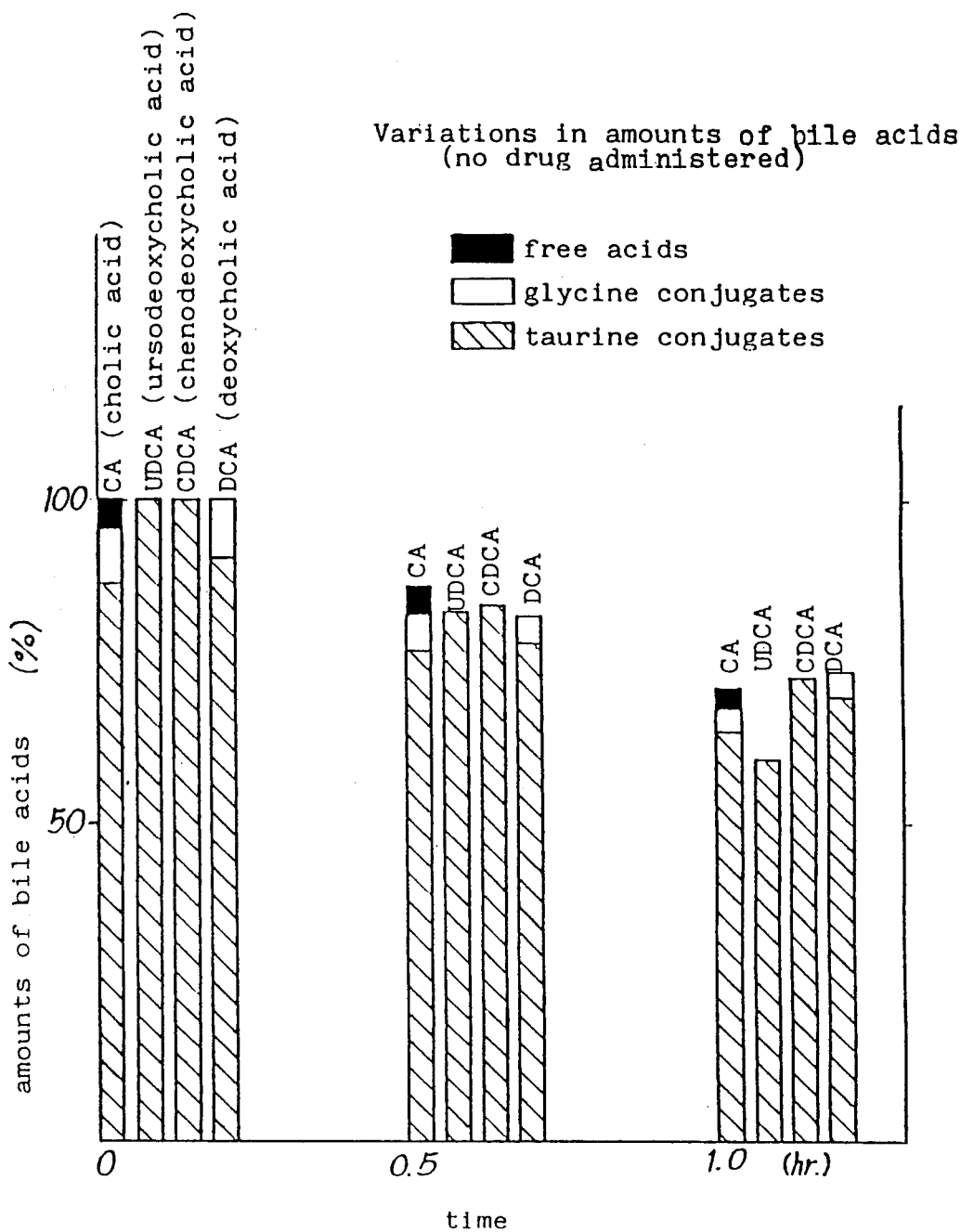
Figure 9:
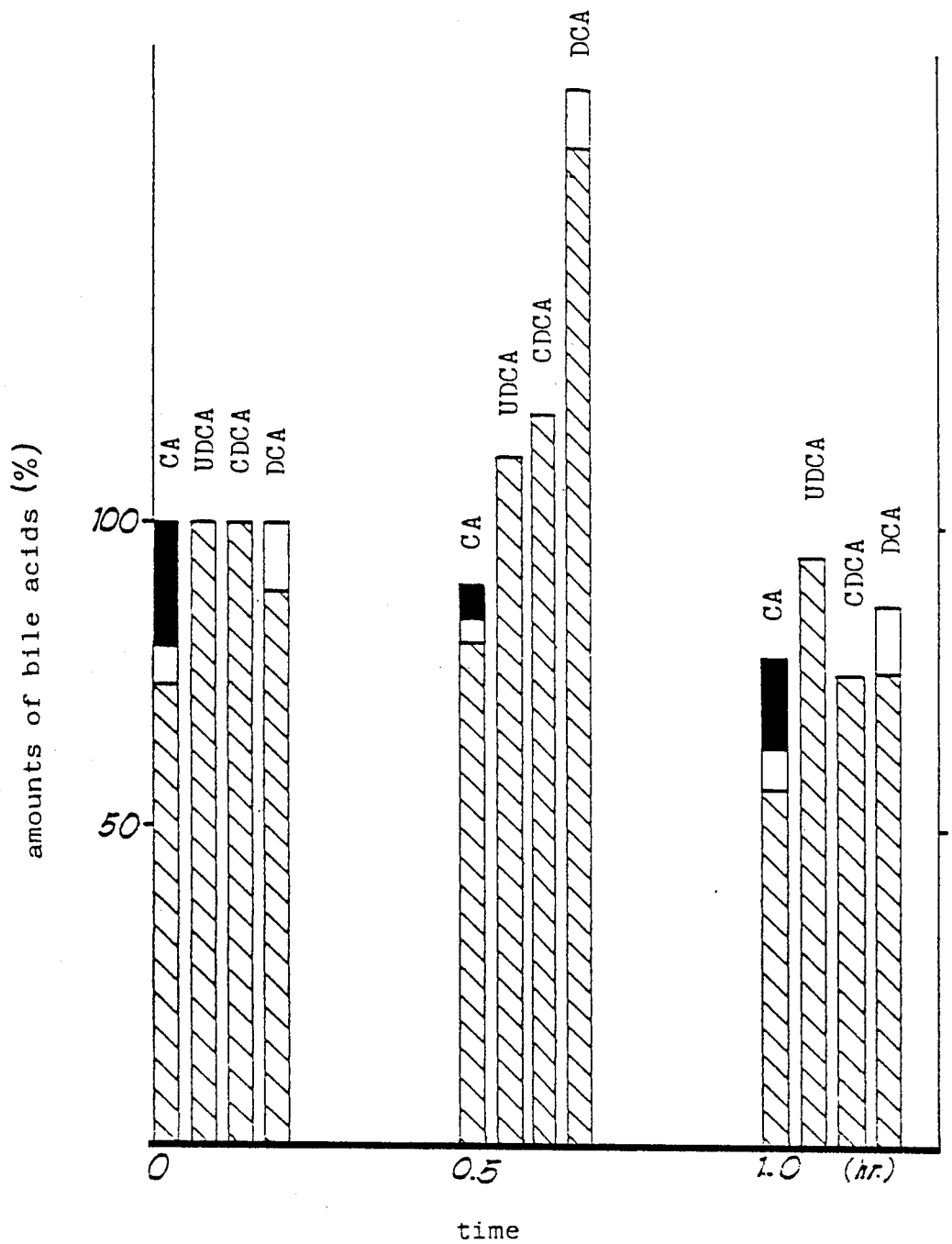
Figure 10:
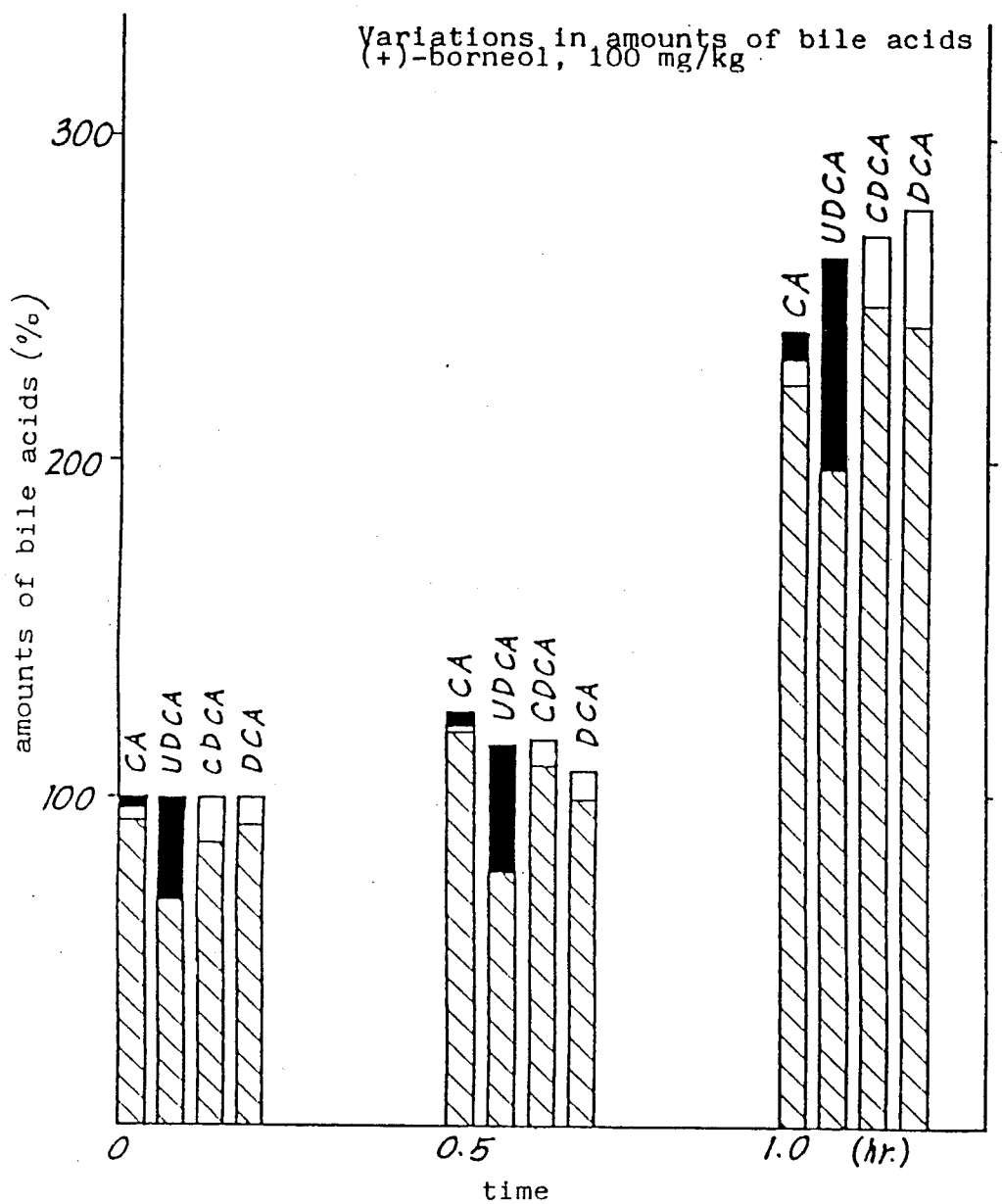

As shown in FIG. 8 to FIG. 10, sodium dehydrocholate exhibited a slight transient tendency to produce increased amounts of bile acids including deoxycholic acid only 30 minutes after the administration, whereas (+)-borneol resulted in secretion of remarkably increased amounts of chenodeoxylic acid and like bile acids.

FIG. 11 further shows that the group to which (+)-borneol was administered exhibited a remarkable increase in the total bile acid content unlike the groups to which no drug was administered or cholagogic sodium dehydrocholate was administered.

The borneol compounds are usable also as gallstone solubilizer.

Human bile contains 2 to 3% of solids in the case of hepatic bile or as much as about 14% of solids in the case of bladder bile, and bile acids account for a major portion of the solid component. Of the components of bile, three are most responsible for the formation of gallstones. These are cholesterol, bile acids and phospholipids. Under the normal condition, cholesterol, which is completely insoluble in water is present as dissolved in micelles composed of bile acids and phospholipids and is discharged safely to the duodenum via the bile duct system. Cholesterol cholelithiasis which has greatly increased in incidence in recent years has been found attributable to the formation of lithogenic bile, i.e. to reduced secretion of bile acids, increased secretion of cholesterol and reduced secretion of phospholipids, which result in supersaturation of bile with cholesterol (Admirand, W. H. and Smalll, D. H., J. Clin. Invest. 47, 1043, 1968). Of these causes, the deficient secretion of bile acids and increase in the relative concentration of cholesterol are most important.

Many people have gallstones among races with supersaturated bile exceedng the limit of dissolution of cholesterol (Nakayama, F. and Van der Linden, W., Am. J. Surg., 122, 8, 1971). On the other hand, the bile of the Masai people in Africa has a high degree of unsaturation with cholesterol, and there is no incidence of gallstones (Ovido, M. A. et al., Arch. Path. Lab. Med. 101, 208, 1977). Further canine bile has a low degree of saturation with cholesterol (Nakayama, F., J. Lab. Clin. Med. 73, 623, 1969). Human gallstones of the cholesterol type, when held inserted in the canine gallbladder, completely dissolves in several months (Nauman, B., Treatise on Cholelithiasis, p. 22, New Sydenham Soc., London, 1896).

With the gallstone formation mechanism thus clarified, the gallstone dissolving therapy by the oral administration of chenodeoxycholic acid or ursodeoxycholic acid has been applied since 1972 (Danzinger, R. G. et al., New Engl. J. Med., 286, 1, 1972; Bell, G. D. et al., Lancet II, 1213, 1972; Isao Makino et al., Japanese Journal Gastroenterol., 72,690, 1975). The experiments on the cholagogic characteristics of borneol compounds have revealed that these compounds remarkably increase the secretion of bile acids such as chenodeoxycholic acid, relatively decrease the concentration of secreted cholesterol and consequently produces bile having a low degree of saturation with cholesterol. This indicates that the borneol compounds are effective for preventing formation of gallstones and dissolving gallstones.

According to the mechanism of activity, cholagogues are classified into choleretics for promoting the secretion of bile from the liver and cholecystagogues for promoting the flow of bile from the gallbladder. The cholagoues of the present invention fall into the former category, i.e. choleretics. Accordingly the present agents are usable for treating diseases of the liver and bile ducts such as cholecystitis, cholangitis, syndromes subsequent to cholecystectomy, hepatitis, chronic liver diseases, jaundice, etc.

Furthermore, the present agents are usable for preventing cholesterol cholelithiasis and also for gallstone dissolving therapy for cholelithiasis due to remaining gallstones, etc.

Acute toxicity test

The drug to be tested was orally given to male dd-Y mice weighing about 20 g, ten mice in each group. The mice were thereafter observed for 7 days to determine the $LD_{50}$ from the number of resulting deaths. During the 7-day observation period, the animals were allowed free access to diets and water. The $LD_{50}$ was determined according to the Litchfield-Wilcoxon method.

Experimental results

|  | $LD_{50}$ (mg/kg, 95% reliability limit) |
| --- | --- |
| (+)− Borneol | At least 10000 |
| Sodium dehydrocholate | 2500 (1923–3250) |

As will be apparent from the foregoing results, the borneol compounds have a structure entirely different from that of sodium dehydrocholate which is a bile acid preparation heretofore chiefly used as a cholagogue and produce a sustained powerful effect. Moreover, these compounds act to dissolve gallstones, are low in toxicity and can be prepared from a material which is readily available because of its low cost. The borneol compounds are administered generally orally and can be formulated into preparations by usual methods, for example, using an excipient such as starch, lubricant such as magnesium stearate or coating agent such as CAP. Such preparations may be in the form of granules, tablets, capsules, etc.

For therapeutic use in adults, a tablet containing 50 to 200 mg of a borneol compound is usually administered at a time, and the dose is administered two to three times a day, whereby a satisfactory efficacy can be achieved. Preparations examples are given below.

EXAMPLE 1

One hundred parts by weight of (+)-borneol and 90 parts by weight of potato starch were thoroughly mixed together, and the mixture was kneaded with water and then passed through a granulator having a screen with 1-mm$^2$ openings. The granules obtained were dried, screened by No. 16 mesh sieve for classification and thereafter mixed with 10 parts by weight of magnesium stearate. The mixture was compressed into 100 mg tablets.

EXAMPLE 2

(+)-Borneol was filled into capsules (No. 4) in an amount of 50 mg in each capsule to obtain an encapsulated preparation.

INDUSTRIAL APPLICATION

The compounds of the present invention are usable as cholagogues and/or gallstone solubilizer.

I claim:

1. A method of increasing the flow of bile comprising administering to patients requiring such treatment a cholagogic effective amount of a borneol compound and a pharmaceutically acceptable diluent.

2. A method of dissolving gallstones comprising administering to patients requiring such treatment a gallstone dissolving effective amount of a borneol compound and a pharmaceutically acceptable diluent.

3. A method of increasing the secretion of bile from the liver, comprising, administering, to patients requiring such treatment, a bile secretion stimulating effective amount of a borneol compound and a pharmaceutically effective diluent.

4. A method as defined in claim 1 wherein the borneol compound is a borneol selected from the group consisting of (+)-borneol, (−)-borneol, (±)-borneol, (+)-isoborneol, (−)-isoborneol and (±)-isoborneol.

5. A method as defined in claim 2 wherein the borneol compound is a borneol selected from the group consisting of (+)-borneol, (−)-borneol, (±)-borneol, (+)-isoborneol, (−)-isoborneol and (±)-isoborneol.

6. A method as defined in claim 3 wherein the borneol compound is a borneol selected from the group consisting of (+)-borneol, (−)-borneol, (±)-borneol, (+)-isoborneol, (−)-isoborneol and (±)-isoborneol.

* * * * *